United States Patent
Spruit et al.

(10) Patent No.: US 12,241,741 B2
(45) Date of Patent: Mar. 4, 2025

(54) LASER SENSOR, SYSTEM AND METHOD FOR SELF-MIXING INTERFEROMETRY

(71) Applicants: TRUMPF Photonic Components GmbH, Ulm (DE); Robert Bosch GmbH, Stuttgart (DE)

(72) Inventors: Hans Spruit, Waalre (NL); Jochen Hellmig, Valkenswaard (NL); Stephan Gronenborn, Aachen (DE); Johannes Meyer, Stuttgart (DE); Andreas Petersen, Stuttgart (DE); Thomas Schlebusch, Stuttgart (DE)

(73) Assignees: TRUMPF PHOTONIC COMPONENTS GMBH, Ulm (DE); ROBERT BOSCH GMBH, Stuttgart (DE)

( * ) Notice: Subject to any disclaimer, the term of this patent is extended or adjusted under 35 U.S.C. 154(b) by 247 days.

(21) Appl. No.: 17/730,220

(22) Filed: Apr. 27, 2022

(65) Prior Publication Data
US 2022/0349703 A1   Nov. 3, 2022

(30) Foreign Application Priority Data
Apr. 30, 2021   (EP) ..................... 21171555

(51) Int. Cl.
*G01B 9/02*    (2022.01)
*G01S 7/4912*  (2020.01)
*H01S 5/00*    (2006.01)

(52) U.S. Cl.
CPC ........ *G01B 9/02092* (2013.01); *G01S 7/4916* (2013.01); *H01S 5/0028* (2013.01)

(58) Field of Classification Search
CPC .. G01B 9/02092; G01B 11/026; G01B 11/26; G01S 7/4916; G01S 7/4814; G01S 17/58;
(Continued)

(56) References Cited

U.S. PATENT DOCUMENTS

2009/0195771 A1\*  8/2009  Ueno ..................... G01S 7/491
                                           356/498
2013/0215410 A1\*  8/2013  Christian .............. G01S 7/4916
                                           356/28.5
(Continued)

FOREIGN PATENT DOCUMENTS

DE   102018214637 A1 \*  3/2020  ............. A61B 3/113
WO   WO-2021049740 A1 \*  3/2021  ........... A61B 3/0025

OTHER PUBLICATIONS

English Translation of Fiess et al. (DE102018214637A1) Description (Year: 2020).\*

(Continued)

*Primary Examiner* — Tarifur R Chowdhury
*Assistant Examiner* — Akbar H. Rizvi
(74) *Attorney, Agent, or Firm* — LEYDIG VOIT & MAYER LTD.

(57) ABSTRACT

A laser sensor includes a laser source configured to emit a laser beam, and optics configured to project the laser beam as a one- or two-dimensional patterned laser beam onto an object to be examined, such that a distance of the patterned laser beam from the laser source varies along the patterned laser beam projected on the object. The laser sensor further includes a detector configured to determine a self-mixing interference signal generated by laser light of the patterned laser beam reflected from the object back into the laser source, and circuitry configured to analyze a spectrum of the self-mixing interference signal and extract from the spectrum of the self-mixing interference signal multiple frequencies that are indicative of at least one of the following: multiple distances along the patterned laser beam from the laser source, or multiple velocities along the patterned laser beam with respect to the laser source.

17 Claims, 10 Drawing Sheets

(58) Field of Classification Search
CPC ........ G01S 17/66; G01S 17/88; H01S 5/0028; G02B 26/0816; G02B 26/0875; G02B 2027/0178; G02B 27/0172; G02B 27/0093; G01P 5/26; G01P 3/36; A61B 3/113; G01J 3/45
See application file for complete search history.

(56) References Cited

U.S. PATENT DOCUMENTS

| | | | | |
|---|---|---|---|---|
| 2017/0147859 | A1* | 5/2017 | Zhang | G06V 40/193 |
| 2017/0302907 | A1* | 10/2017 | Wallius | H04N 5/33 |
| 2019/0285753 | A1* | 9/2019 | Spruit | G01S 7/497 |
| 2020/0374620 | A1* | 11/2020 | McCord | H04R 1/1041 |
| 2021/0271320 | A1 | 9/2021 | Fiess et al. | |

OTHER PUBLICATIONS

Taimre, et al., "Laser Feedback Interferometry: A Tutorial on the Self-Mixing Effect for Coherent Sensing," Advances in Optics and Photonics 7, 3, pp. 570-631, Aug. 20, 2015, Optica Publishing Group, Washington DC, USA.

* cited by examiner

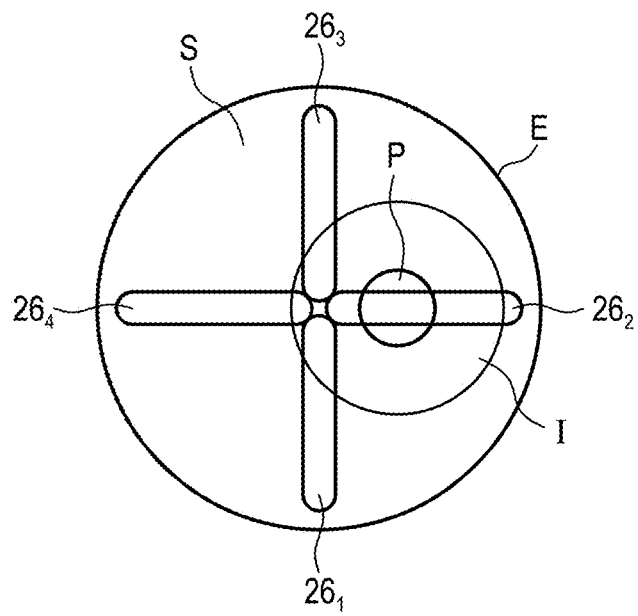
Fig. 15
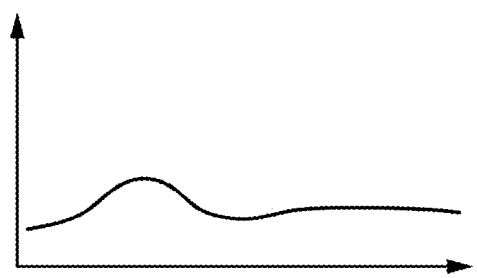 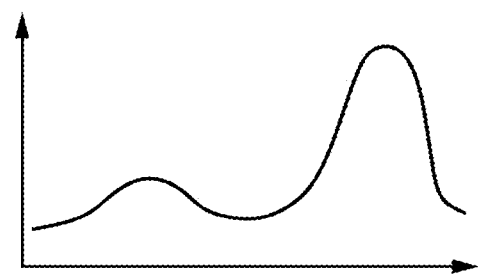
Fig. 16a)          Fig. 16b)

LASER SENSOR, SYSTEM AND METHOD FOR SELF-MIXING INTERFEROMETRY

CROSS REFERENCE TO RELATED APPLICATIONS

This application claims benefit to European Patent Application No. EP 21171555.2, filed on Apr. 30, 2021, which is hereby incorporated by reference herein.

FIELD

Embodiments of the present invention relate to the field of detecting position and velocity of an object using self-mixing interference measurements.

BACKGROUND

Self-mixing interference (SMI) is a technique to obtain distance and velocity information from objects. Laser light emitted by a laser source, e.g. a laser diode, in particular a vertical cavity surface emitting laser (VCSEL), is directed to an object of which, e.g., the velocity and/or position needs to be determined, and laser light reflected from the object re-enters the laser source and interferes with the optical wave within the laser resonator. This results in intensity variations that are sensed by a detector, e.g. a photodiode, which may be integrated in the structure of the laser source.

SMI can be applied in e.g. mouse sensors, distance sensors, speed over ground applications, particle detection, etc.

Recently, SMI was proposed for tracking the gaze of a human eye. Tracking the different positions of a human eye may be beneficial in several applications, e.g. in head-mounted displays, head-up displays, and data glasses. Text or images are to be displayed at a position of the display which corresponds to the gaze of the user. In present techniques of eye tracking, apart from the SMI sensor, a camera system is needed as well to derive explicit eye positions. Thus, conventional systems are disadvantageous in terms of costs and complexity.

It is to be noted that embodiments of the present invention are not limited to eye gaze angle detection, but may be implemented in a variety of other applications, where position and/or velocity information is to be obtained from an object. The term "object" not only encompasses solid objects, but also fluid objects. Further, the term "an object" may also encompass a plurality of objects.

SUMMARY

Embodiments of the present invention provide a laser sensor. The laser sensor includes a laser source configured to emit a laser beam, and optics configured to project the laser beam as a one- or two-dimensional patterned laser beam onto an object to be examined, such that a distance of the patterned laser beam from the laser source varies along the patterned laser beam projected on the object. The laser sensor further includes a detector configured to determine a self-mixing interference signal generated by laser light of the patterned laser beam reflected from the object back into the laser source, and circuitry configured to analyze a spectrum of the self-mixing interference signal and extract from the spectrum of the self-mixing interference signal multiple frequencies that are indicative of at least one of the following: multiple distances along the patterned laser beam from the laser source, or multiple velocities along the patterned laser beam with respect to the laser source.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following:

FIG. 15 shows laser beams of four laser sensors which are projected as two-dimensional patterned laser beams on the surface of the eye after eye rotation according to some embodiments;

FIG. 16a) and FIG. 16b) show measured frequency spectra for two sensing regions on the surface of the eye in the rotational position according to FIG. 15, wherein FIG. 16a) shows a frequency spectrum of a first sensing region and FIG. 16b) shows a frequency spectrum of another sensing region, according to some embodiments;

DETAILED DESCRIPTION

Figure 1:
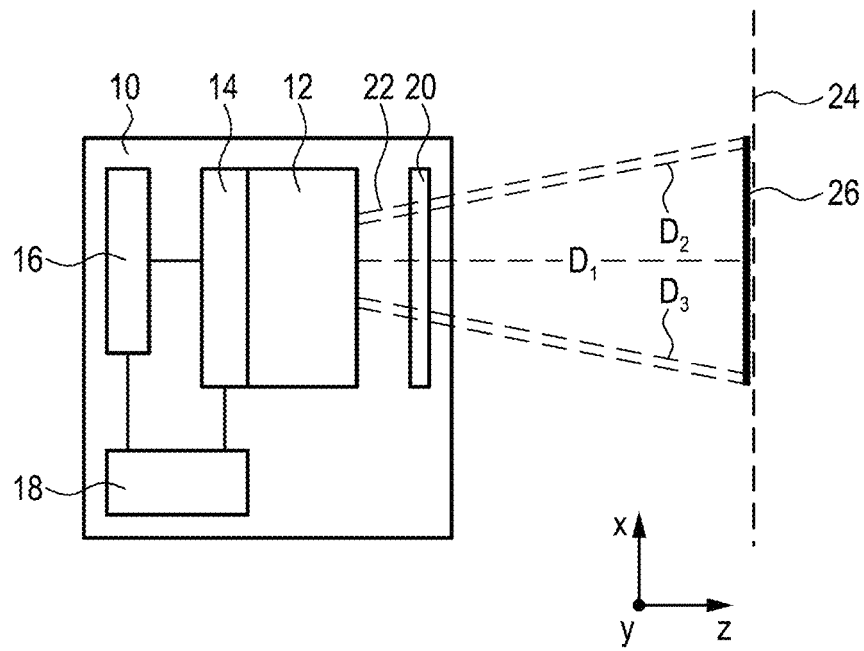
FIG. 1 shows a sketch of a laser sensor.

Embodiments of the present invention provide a laser sensor which is capable of performing self-mixing interference measurements without the need for additional systems, such that all position and/or velocity information needed can be obtained from the self-mixing interference measurement.

Embodiments of the present invention provide a system capable of detecting at least one of a position or velocity of an object with high accuracy without the need for additional systems like a camera.

According to a first aspect of the present invention, a laser sensor is provided. The laser sensor comprising a laser source configured to emit a laser beam, optics configured to project the laser beam as a one- or two-dimensional patterned laser beam onto an object to be examined, such that a distance of the patterned laser beam from the laser source varies along the patterned laser beam projected on the object, a detector configured to determine a self-mixing interference signal generated by laser light of the patterned laser beam reflected by the object back into the laser source, and circuitry configured to spectrally analyze the self-mixing interference signal and extract from the spectrum of the self-mixing interference signal multiple frequencies indicative of multiple distances along the patterned laser beam from the laser source and/or multiple velocities along the patterned laser beam with respect to the laser source.

The laser source according to embodiments of the present invention enables obtaining more information from the self-mixing interference signal as conventional SMI laser sensors. This is achieved by two differences with respect to conventional SMI techniques. A first difference is making use of a one- or two-dimensional patterned laser beam hitting the object to be examined. In contrast, in conventional SMI techniques, a laser beam is projected as a single point-like beam spot on the object so that there is only one distance of the laser beam spot on the object from the laser source at one point of time. By projecting the laser beam as a one- or two-dimensional patterned laser beam onto the object such that a distance of the patterned laser beam from the laser source varies along the patterned laser beam projected onto the object, there are multiple distances of the patterned laser beam from the laser source at one point of time. Thus, the back-reflected patterned laser beam generates an SMI signal which contains much more position and/or velocity information based on this multitude of distances than in case of a SMI signal based on a single beam spot projected on the object.

"One- or two-dimensional patterned beam" means that the projected laser beam has an extension in one or two dimensions. A one-dimensional patterned laser beam may be a straight or curved line or stripe, for example. The line may be a continuous line, a broken line, or a plurality of dots arranged in a line. A one-dimensional patterned beam may be characterized by a beam width in a first direction which is at least two times the beam width in a second direction perpendicular to the first direction. A two-dimensional patterned laser beam may have a beam profile extending over an area with at least one minimum of laser light intensity within the area, wherein the minimum may be zero. For example, a two-dimensional patterned beam may be a circle, ellipse, rectangle, a grid of a plurality of lines, a cross, etc.

The emitted laser beam may comprise a plurality of laser beams emitted by the laser source. A plurality of laser beams may be emitted in time-multiplexed manner. The laser source may comprise a single laser or a plurality of lasers. The laser source may comprise a single laser comprising a plurality of laser beam emission regions. For example, the laser may be a VCSEL array having two or more mesas, each mesa being a laser beam emission region.

A second difference between the laser sensor according to embodiments of the present invention and the conventional SMI laser sensors is that the laser sensor according to embodiments of the present invention spectrally analyses the self-mixing interference signal and extracts from the spectrum, e.g. the full spectrum or at least an essential part of the spectrum, multiple frequencies which are indicative of multiple distances along the patterned laser beam from the laser source and/or multiple velocities along the patterned laser beam with respect to the laser source. In conventional SMI laser sensors, only a peak frequency in the SMI signal is used to obtain position and/or velocity information from the SMI signal. By making use of spectral analysis of the SMI signal, much more and in particular more accurate information may be obtained from the SMI signal. The spectral analysis of the SMI signal may be performed in the frequency domain or in the time domain. For instance, after a Fast-Fourier Transformation (FFT) of the SMI signal, the information in a plurality of, or even in all bins, is used according to embodiments of the present invention.

Instead of getting one velocity and/or one distance as in case of conventional SMI sensors, a whole spectrum of information is available from which multiple distances and velocities can be analyzed simultaneously according to embodiments of the present invention.

The laser sensor according to embodiments of the present invention is particularly, but not exclusively, suitable for eye gaze angle detection. There is no need for an additional camera anymore. The laser sensor according to embodiments of the present invention is also particularly, but not exclusively, suitable for velocity profile detection in a flowing fluid, or for tilt detection of an object. Embodiments of the present invention provide a very cost effective and power effective solution to introduce spatial resolution over conventional systems using an array of a multitude of traditional SMI sensors.

The laser source of the laser sensor may be a laser diode, in particular a VCSEL. The detector may be configured as a photodiode integrated into the VCSEL, e.g. as an intra-cavity photodiode or an extra-cavity photodiode.

Exemplary embodiments of the present invention are defined in the dependent claims and as further indicated herein.

In an embodiment, the laser sensor comprises an electrical driver configured to provide a driving current to the laser source to cause the laser source to emit the laser beam, wherein the electrical driver may be configured to provide a modulated driving current to the laser source to cause the laser source to emit the laser beam with a periodically varying wavelength.

The periodically varying wavelength influences the self-mixing interference signal. If the object to be examined does not move, using a modulated laser beam with periodically varying wavelength enhances the accuracy of the detection of multiple positions. In case of a moving object, a triangular modulated laser beam results in different frequencies of the SMI signal for the rising and trailing (falling) edge, wherein the mean of both frequencies is an indicator of object distance, while the difference correlates with the double Doppler frequency of the SMI signal.

The pattern of the patterned laser beam projected onto the object may be selected from the group consisting of a continuous-line pattern, a dot-line pattern, a multiple-line pattern. For example, the patterned laser beam may be a straight or curved line or stripe, including a closed line like a circle, ellipse, rectangle, a grid, a cross, etc.

In a further embodiment, the optics is further configured to focus the patterned laser beam onto the object. Focusing the patterned laser beam onto the object advantageously increases the SMI signal strength, or in other words the signal-to-noise ratio (SNR). It is preferred to have the best focus position as best as possible matching the position of the surface of the object to be examined for optimum SMI signal. The optics may be adapted to project the laser beam such that the focus position is optimized at the surface of the object. This is of particular benefit, if the object has a non-planar surface.

The optics may be selected from the group consisting of a single cylinder lens, two or more crossed cylinder lenses, a cylinder lens having cylindrical surfaces with different orientations of cylinder axes of the cylindrical surfaces, free form optics, meta optics, diffractive elements, e.g. one or more optical gratings, holographical optics, mirrors, which may be spherical, cylindrical or free-form mirrors, wherein the mirrors may be partially reflecting.

Depending on the object to be examined, the optics may be chosen, accordingly, in particular to optimize the best focus position along the patterned laser beam.

According to a second aspect, a system for detecting at least one of a position or velocity of an object is provided, comprising a laser sensor according to the first aspect. As the system comprises a laser sensor according to embodiments of the present invention, the system can measure multiple positions and/or velocities with a single laser sensor.

The system may further comprise at least a second laser sensor comprising a second laser source configured to emit a second laser beam and second optics configured to project the second laser beam as a one- or two-dimensional patterned laser beam onto the object, wherein the patterned laser beam and the second patterned laser beam intersect on the object under a non-zero angle.

The non-zero angle may be 90° or an obtuse or acute angle. Using two patterned laser beams projected onto the object is advantageous, if the object can move in different directions.

The object to be examined may be a human eye, and the system may be configured to detect the gaze angle of the eye.

Detection of the gaze angle of the eye may be performed by analyzing the spectrum of the SMI signal for a gap in the spectrum which is indicative of the position of the pupil of the eye, as the patterned laser beam or a part thereof is, at the pupil position, dominantly reflected at the retina which has a larger distance from the laser source than the front surface (iris and sclera) of the eye. The system for eye gaze angle detection may be configured to project multiple patterned laser beams onto the eye in time-multiplexed manner.

The system according to embodiments of the present invention may also be configured to detect a tilt angle of an object. Detection of tilt of an object may be used in any applications, for example in quality control of products in a production line. Tilt detection may also be used to detect the gaze angle of the eye, as the tilt of the iris is a measure for the eye gaze angle.

The system may also be configured to detect a velocity profile of a flowing fluid. This is an embodiment of analyzing the spectrum of the SMI signal to extract multiple velocities along the patterned laser beam with respect to the laser source. For example, micro-particles in the fluid may reflect the patterned laser beam, generating a measurable SMI signal. In this case, it is preferred to have SMI signals from the focused position of the patterned laser beam only, so that it is preferred to have a relatively large numerical aperture at the fluid side for optimal position discrimination.

According to a third aspect, a method is provided, comprising emitting a laser beam from a laser source, projecting the laser beam as a one- or two-dimensional patterned laser beam onto an object to be examined, such that a distance of the patterned laser beam from the laser source varies along the patterned laser beam projected on the object, determining a self-mixing interference signal generated by laser light of the patterned laser beam reflected from the object back into the laser source, spectrally analyzing the self-mixing interference signal and extracting from the spectrum of the self-mixing interference signal multiple frequencies indicative of multiple distances along the patterned laser beam from the laser source and/or multiple velocities along the patterned laser beam with respect to the laser source.

According to a fourth aspect, a computer program product comprising program code means for causing a laser sensor according to the first aspect or a system according to the second aspect to carry out the steps of the method according to the third aspect, when said computer program is carried out on a processor of the laser sensor or on a processor of the system.

Further advantageous embodiments are defined below.

Before referring to the drawings, the principles of self-mixing interference and laser sensor basics are explained.

The operating principle of a laser, e.g. a laser diode, e.g. a vertical cavity surface emitting laser, is based on optical resonators. Inside of the resonator, electrons are in exited state by external energy input. Radiation by spontaneous emission is reflected forth and back in the optical resonator and causes a stimulated emission, thus amplifying the resonant mode and producing coherent radiation. At one side of the lasing cavity, laser radiation can couple into free-space through a semi-transparent mirror. In case of a vertical cavity surface emitting Laser (VCSEL), the mirror structures are realized as distributed Bragg reflectors (DBR). A photodiode may be placed in the VCSEL, wherein the photodiode may be integrated into the lasing cavity, or may be placed outside the lasing cavity. Thus, a VCSEL with integrated photodiode, abbreviated as ViP, is formed.

The underlying physical effect of laser self-mixing is explained next. A beam laser emitted by the laser may be reflected at an object. "Reflected" as used herein is not only understood as specular reflection, but also as diffuse reflection, also referred to as scattering. If externally reflected laser radiation couples back into the laser cavity, stimulated emission in the laser cavity is modulated based on the phase of back-scattered photons. If twice the distance between laser cavity and external scattering surface (back and forth) equals an integer multiple of the wavelength of the laser light, scattered radiation and radiation inside of the laser resonator are in phase. This results in positive interference, whereby lasing threshold is reduced and laser output is slightly increased, which may be sensed by the photodiode integrated into the laser. At slightly increased distance, both radiation waves are out of phase and at some point negative interference occurs, reducing laser output power. If the distance to the scattering surface of the object is changed at constant speed, laser output power is oscillating between a maximum during constructive interference and a minimum during destructive interference. The resulting oscillation is a function of the speed of the scatterer (object) and laser wavelength.

The same effect, namely oscillating laser output power, can be observed if the distance between the laser cavity and the scattering surface is left constant, but the laser wavelength is changed. Laser wavelength change may be achieved by modulating the external energy, e.g. a driving current, used for driving the laser. Now, the phase of radiation between internal cavity inside the laser and external cavity between laser and scatterer is dependent on how many wavelengths "fit" inside the external cavity. However, the frequency of oscillation of output power is dependent on distance between laser and scattering surface, as the wavelength of the laser light typically is in the near infrared region, e.g. around 850 nm, and external cavity distances are in the region of several centimeters, so that slight change in laser wavelength can result in a full turn of external cavity laser phase. The higher the distance between laser and scattering surface, the less wavelength change results in a full turn of external cavity laser phase. Assessing the laser output power variation, the higher the distance to the scatterer, the higher the power variation frequency at constant laser wavelength change. Therefore, mapping the power monitoring photodiode into frequency domain, the peak frequency correlates with the distance between laser and scatterer. Laser wavelength change can be introduced by power modulation of the laser diode. For example, a driving current may be linearly modulated according to a triangular laser current.

If both effects superimpose, i.e. laser wavelength is modulated and scatterer moves, resulting beat frequencies as known from frequency modulated continuous wave radar systems occur. Due to the Doppler shift in frequency, the resulting beat frequency is lower for a target moving towards the laser sensor during ramp up of the frequency (according to the wavelength modulation) and higher during ramp down of the frequency. Thus, beat frequencies are to be calculated for rising and falling modulation segments individually. The mean of both frequencies is an indicator for object distance, while the difference correlates with the double Doppler frequency.

Next, with reference to FIG. 1, a laser sensor will be described. FIG. 1 shows a sketch of a laser sensor 10. The laser sensor 10 comprises a laser source 12 and a detector 14. The detector 14 may be integrated with the laser source 12. More specifically, the detector 14 may be a photodiode integrated into the layer structure of the laser source 12, wherein the photodiode may be integrated as an intra-cavity photodiode or an extra-cavity photodiode. The laser sensor 10 may further comprise an electrical driver 16 and a controller 18. The controller 18 is connected to the laser source 12 including the photodetector 14. The electrical driver 16 supplies electrical power to the laser source 12 to cause the laser source 12 to emit a laser beam 22, indicated by broken lines. The laser source 12 may be or comprise a vertical cavity surface emitting laser (VCSEL) with integrated photodiode, i.e. a ViP. The electrical driver 16 may be configured to provide a constant driving current or a modulated driving current to the laser source 12. In case the electrical driver 16 provides modulated driving current to the laser source 12, the modulated driving current may follow a triangular shape. The controller 18 is further configured to receive electrical signals provided by the detector 14 which are caused by self-mixing interference (SMI) of laser-light re-entering the laser cavity with laser light generated in the laser cavity.

The laser sensor 10 further comprises optics 20. The optics 20 is configured to project the laser beam 22 as a one- or two-dimensional patterned laser beam onto an object 24 to be examined. The object 24 is illustrated in FIG. 1 by a broken line, wherein the broken line resembles the reflecting (scattering) surface of the object 24.

Figure 2A:
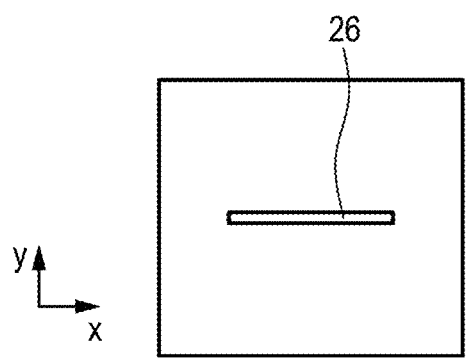
FIG. 2a) and FIG. 2b) show examples of patterned laser beams projected on an object.
Figure 2B:
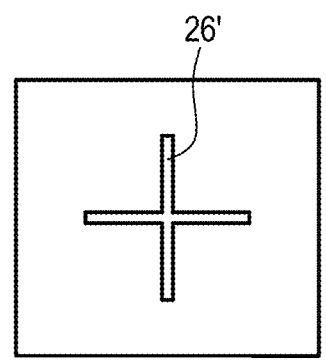

Optics 20 is configured to project the laser beam as a one- or two-dimensional patterned laser beam 26 onto the object 24 to be examined such that a distance D of the patterned laser beam 26 from the laser source 12 varies along the patterned laser beam 26 projected onto the object 24. In FIG. 1, three distances $D_1$, $D_2$, $D_3$ are exemplarily shown, wherein $D_2$ and $D_3$ are larger than $D_1$. An example of a patterned laser beam 26 is shown in FIG. 2a). The patterned laser beam 26 in FIG. 2a) is a line shaped beam, as an example for a one-dimensional projected patterned laser beam. FIG. 2b) shows a crossed-line beam, as an example for a two-dimensional projected patterned laser beam. In general, the pattern of the projected patterned laser beam may be selected from the group consisting of a continuous-line pattern, as shown in FIG. 2a), a dot-line pattern, which is a line comprising discrete dots, a grid of continuous lines or dot lines, A pattern as the crossed-line beam 26' shown in FIG. 2b) may be achieved by using two laser sources 12 and corresponding optics 20, wherein the latter may comprise two crossed cylinder lenses, one for each laser source, or an array of micro-lenses, wherein two subsets of lenses are orthogonal to each other.

The optics may be further configured to focus the patterned laser beam 26 onto the object 25. The patterned laser beam 26 may be focused in direction of a first dimension only, e.g. the y-dimension in FIG. 2a). The cross 26' in FIG. 2b) may be focused in each of the short dimensions of the two crossing lines.

The optics 20 may be further configured to expand the laser beam 22 emitted by the laser source 12 in one or two dimensions. For example, the patterned laser beam 26 in FIG. 1 may have been expanded by the optics 20 to expand the long dimension of the patterned laser beam 26. It is, however, also possible that the long dimension of the patterned laser beam 26 is achieved by the divergence of the laser beam 22 emitted by the laser source 12 without any additional expansion in the long dimension, for example if the object distance from the laser source is large enough.

Figure 3:
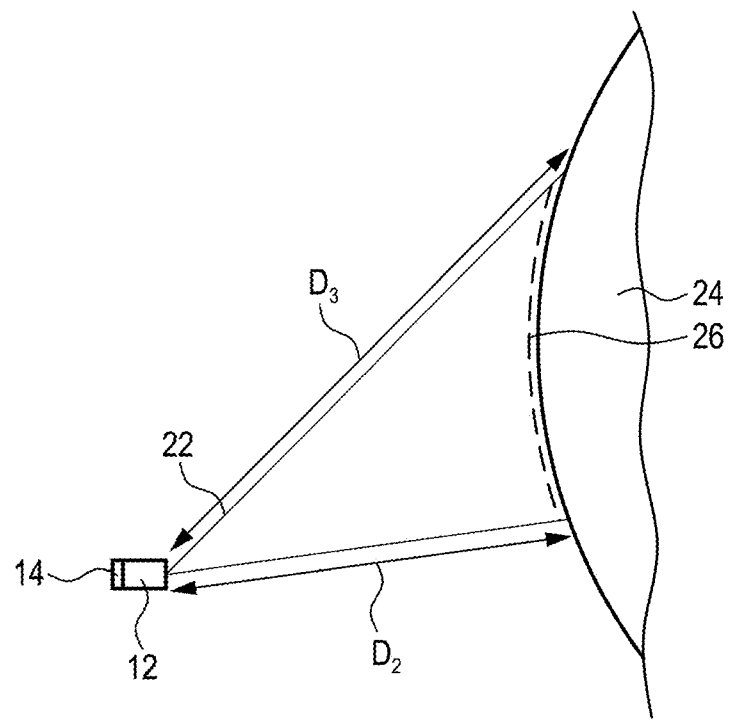
FIG. 3 shows a sketch of a laser sensor emitting a laser beam projected as patterned laser beam onto an object having a non-planar surface.
Figure 6:
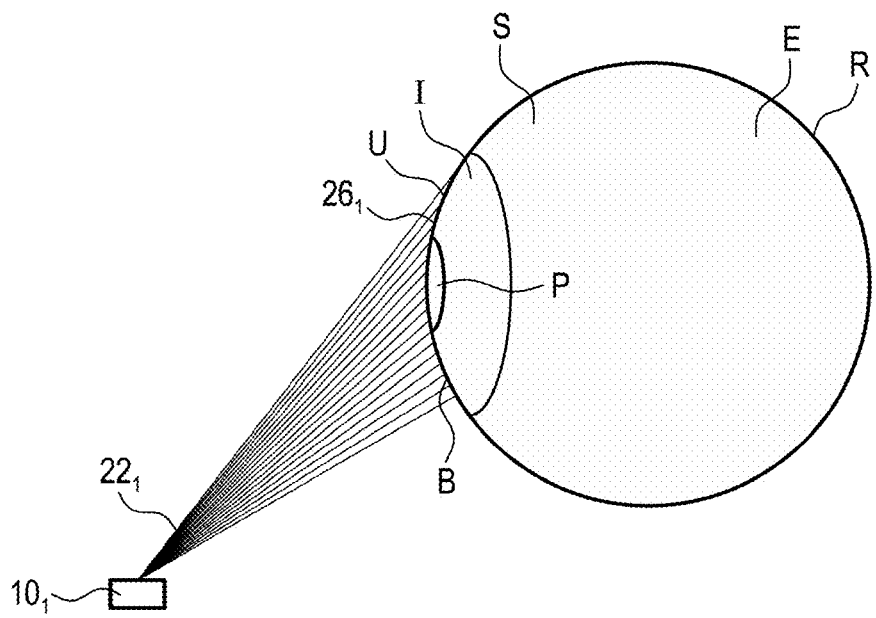
FIG. 6 shows a side view of one of the patterned line shaped beams falling on the eye according to some embodiments.

Further, the optics 22 may be arranged to obliquely project the laser beam 22 onto the object 24, as shown in FIGS. 3 and 6. As shown in FIG. 3, the object 24 may further have a non-planar surface. With an oblique projection of the laser beam 22, the distance D of the patterned laser beam 26 from the laser source 12 stronger varies along the patterned laser beam 26 even for a planar object surface than in a symmetrical projection as shown in FIG. 1.

Figure 4:
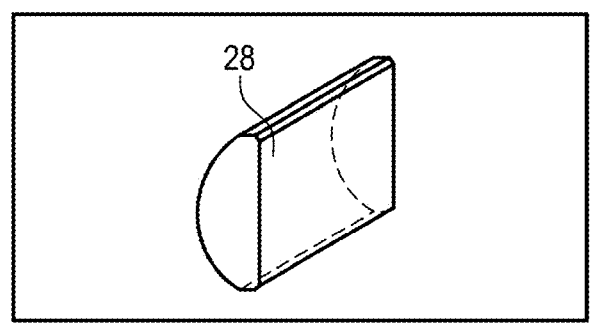
FIG. 4 shows an example of optics for use in the laser sensor in FIG. 1.

The optics 22 may comprise one or more optical elements. An example of optics 22 is shown in FIG. 4, wherein the optics comprises a cylinder lens 28. In general, the optics 22 may be selected from the group consisting of a single cylinder lens, two or more crossed cylinder lenses, a cylinder lens having cylindrical surfaces with different orientations of cylinder axes of the cylindrical surfaces, free form optics, meta optics, one or more optical gratings, holographical optics, mirrors. Crossed cylinder lenses may be used, for example, to project and focus the laser beam $22$ in form of a crossed line shape as shown in FIG. $2b$) when two laser sources are used, or to tune the line length independently from the line width.

With reference back to FIG. 1, the detector 14 is configured to determine a self-mixing interference signal generated by laser light of the patterned laser beam 26 reflected by the object 24 back into the laser source 14. The laser sensor 10 further comprises circuitry configured to spectrally analyze the self-mixing interference signal and extract from the spectrum of the self-mixing interference signal multiple frequencies indicative of multiple distances (e.g. distances $D_1, D_2, D_3$) along the patterned laser beam 26 from the laser source 12 and/or multiple velocities along the patterned laser beam 26 with respect to the laser source 12, as described herein.

The afore-mentioned function of the circuitry may be performed by the controller 18 of the laser sensor 10.

With reference to FIGS. 5 to 9, an embodiment of the laser sensor for eye gaze angle detection will be described.

Figure 5:
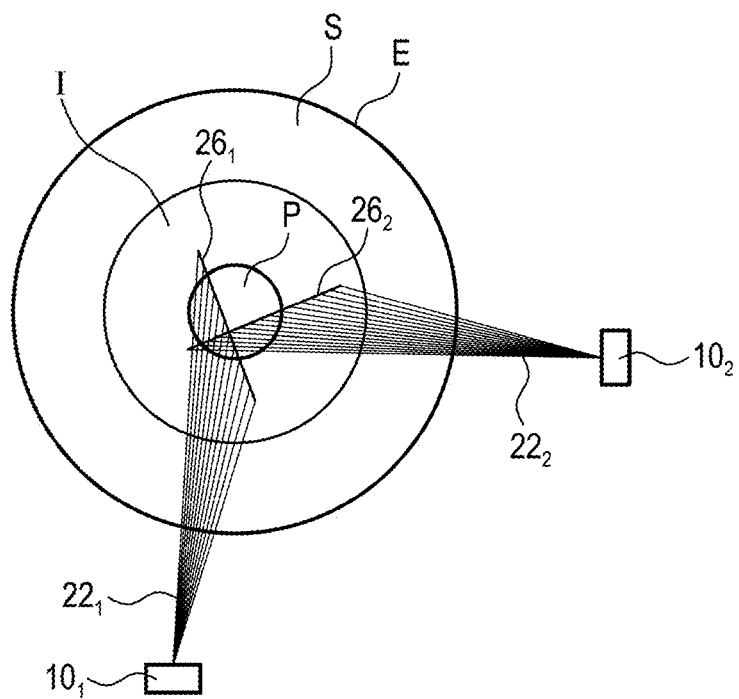
FIG. 5 shows a schematic front view with two orthogonally patterned line shaped beams falling under an angle on a human eye according to some embodiments.

FIG. 5 schematically shows a front view of a human eye E. P denotes the pupil of the eye E, I the iris of the eye, and S the sclera of the eye E. A first laser sensor $10_1$ emits a laser beam $22_1$ which is projected by optics like optics 20 in FIGS. 1 and 4 as a line shaped laser beam $26_1$ onto the surface of the eye E. A second laser sensor $10_2$ emits a second laser beam $22_2$ which is projected by optics as a line shaped laser beam $26_2$ onto the surface of the eye E. The patterned laser beam $26_2$ may be orthogonal to the patterned laser beam $26_1$. The optics used for projecting the laser beam $22_1$ and $22_2$ onto the eye E may be a cylinder lens in each case, one cylinder lens of the laser sensor $10_1$ and one cylinder lens of the laser sensor $10_2$. FIG. 6 shows a side view of the eye E, wherein only the laser beam $22_1$ emitted by the laser sensor $10_1$ and the patterned (line shaped) projected laser beam $26_1$ are shown.

As shown in FIG. 6, the laser beam $22_1$ is obliquely projected onto the eye E in the region of the pupil E. The patterned laser beam $26_1$ has an extension along its long dimension which preferably is larger than the pupil diameter.

The laser beams $22_1$ and $22_2$ are emitted as modulated laser beams, wherein the laser sources of laser sensor $10_1$ and $10_2$ are supplied with modulated driving current. In the present embodiment, a triangular modulation is used. Due to the wavelength variations, the phase of the laser light reflected from the eye E will vary, resulting for one fixed distance in one fixed frequency. However, having the laser beam $26_1$ projected onto the eye E as shown in FIG. 6, multiple different frequencies will be detected in the self-mixing interference signal, as the distance between the projected patterned laser beam $26_1$ and the laser source $10_1$ varies along the projected patterned laser beam $26_1$.

The SMI signal determined by the detector 14 (FIG. 1) which is generated by laser light of the patterned laser beam $26_1$ reflected by the eye E back into the laser source 12 of the laser sensor $10_1$ thus comprises multiple frequencies corresponding to multiple distances along the patterned laser beam $26_1$ from the laser source 12 of the laser sensor $10_1$.

The same distance variations and thus multiple frequencies are measured by the second laser sensor $10_2$ along the patterned laser beam $26_2$ on the surface of the eye E.

Figure 7:
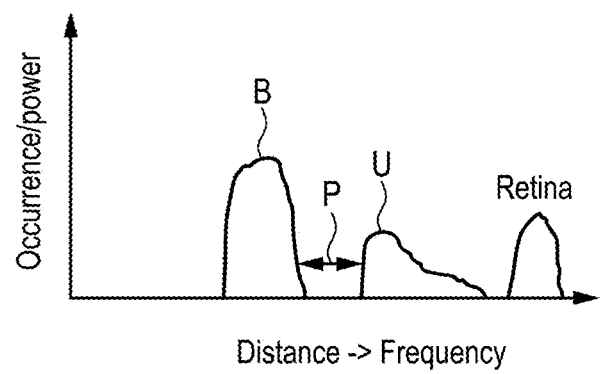
FIG. 7 shows a sketch of a spectrum resulting from the projected patterned line shaped beam as shown in FIG. 6, according to some embodiments.

When part of the patterned laser beam $26_1$ enters the pupil P, laser light travels further to the retina R. Since the distance of the retina R from the laser source 12 of the laser sensor $10_1$ is larger than the distance of the iris I and sclera S from the laser source 12 of the laser sensor $10_1$, a gap is expected in the SMI spectrum. The position of this frequency gap is an absolute measure for the pupil P position. This will be explained with reference to FIGS. 7 and 8. FIG. 7 shows a spectrum of the SMI signal resulting from the projected patterned laser beam $26_1$ in FIG. 6. The horizontal axis of the diagram in FIG. 7 shows the SMI signal frequency. SMI signal frequency may be translated into distance as explained above. The vertical axis in FIG. 7 shows the power or occurrence of the SMI signal in dependence on SMI signal frequency. SMI signals with low frequencies belong to low distances, corresponding to bottom part B (FIG. 6) of the projected patterned laser beam $26_1$. At the pupil position, the patterned laser beam $26_1$ is reflected at the retina, corresponding to large distances/frequencies. Medium frequencies correspond to the upper part U of the patterned laser beam $26_1$. There is a gap between the lower frequencies corresponding to the part B and the medium frequencies corresponding to the part U which gap corresponds to the position of the pupil P. Thus, the pupil position may be accurately measured.

If the eye E moves, i.e. rotates, and thus the gaze angle moves, the gap position (P in FIG. 7) in the spectrum shifts due to the change in "missing" distance from the pupil location. The proper and exact pupil position may then be derived after averaging the gap positions in the spectrum on the rising and the falling edge of the triangle wavelength modulation of the laser beam $22_1$.

In order to verify the above, experiments have been performed using an artificial eye. The artificial eye is a 3D-printed sphere with a hole, representing the pupil. A laser beam is projected as a line shaped patterned laser beam on this artificial eye, using a f=20 mm cylinder lens with 2 f-2 f imaging. Triangle modulation from an external function generator with a modulation frequency of 8 kHz with a modulation laser current amplitude of 0.51 mApp is performed. The average laser power is 0.5 mW.

Figure 8:
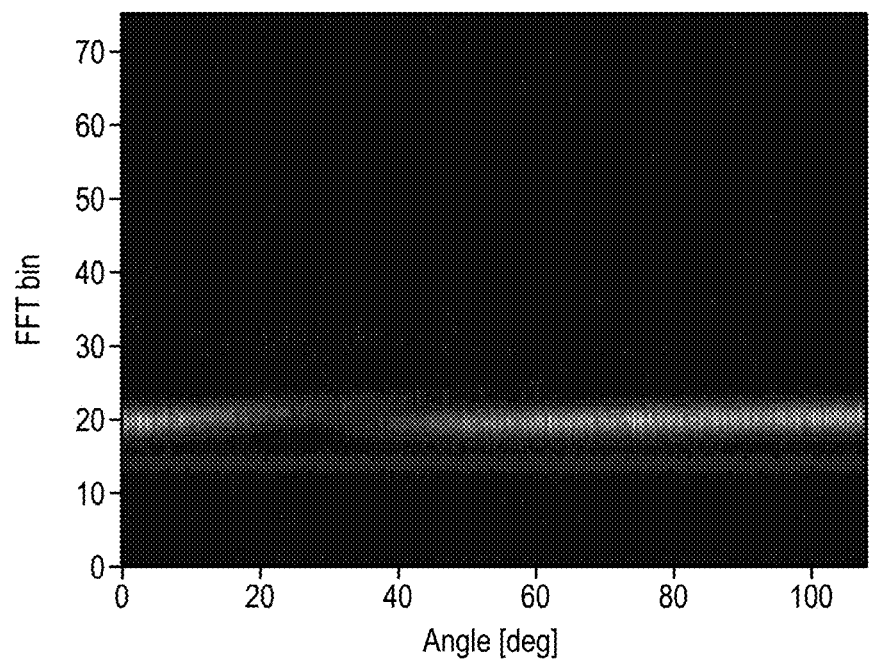
FIG. 8 shows a FFT spectrum as a function of the relative rotation angle in an experiment on an artificial eye according to some embodiments.

FIG. 8 shows the result of this experiment. The artificial eye is rotated clockwise in the sketch of FIG. 6. When the pupil P passes the projected patterned laser beam, low distances/frequencies disappear first, and upon further rotating the artificial eye, finally the high frequencies disappear. After the pupil P passed the patterned laser line beam, all frequencies are visible again. FIG. 8 shows an FFT spectrum as a function of relative rotation angle of the artificial eye. At around 30 degrees, the pupil P is passing the projected laser line beam, resulting in a dip in the power at these frequencies (bin 20 in FIG. 8). The signal line at FFT bin 14 is an artefact caused by a reflection of some dirt on the cylinder lens front surface.

Figure 9:
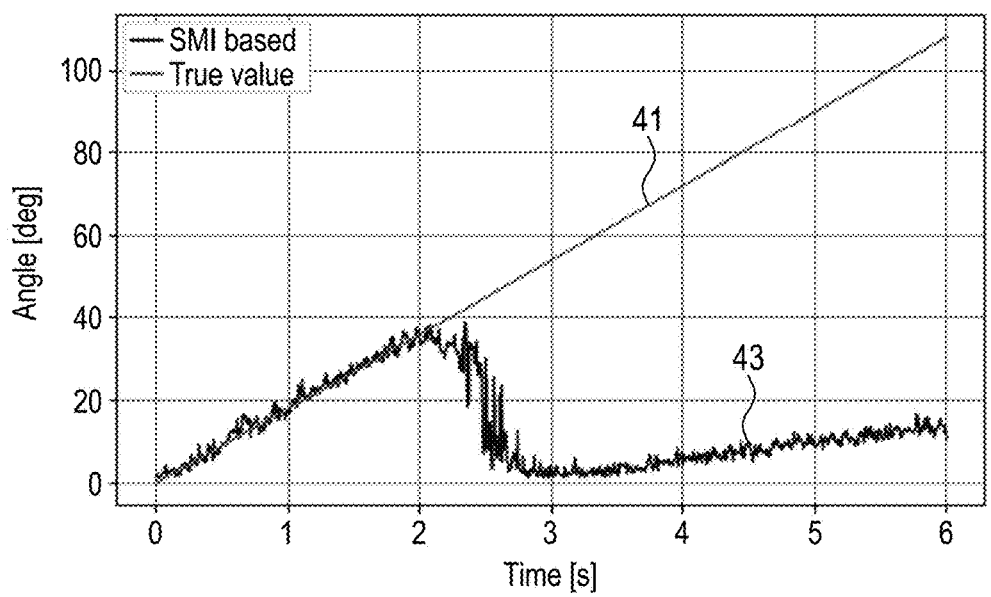
FIG. 9 shows reconstructed eye gaze angle for the experiment on the artificial eye according to some embodiments.

From this experiment, it can be understood that the orientation or gaze angle of the eye can be reconstructed from the measured SMI signal by spectral analysis of the SMI signal in the angle range where part of the laser light is falling in the pupil. Reconstruction may be done using a feed-forward neural network, wherein the result of this reconstruction is shown in FIG. 9. FIG. 9 shows the reconstructed eye gaze angle for the experiment on the artificial eye, showing the eye angle as a function of time. The straight line 41 is the true value of the eye gaze angle, and the curve 43 is the SMI based measured value of the eye gaze angle. FIG. 9 shows that the eye gaze angle can be correctly reconstructed in the range with unique spectral signatures, which means up to two seconds. After two seconds, the pupil P of the artificial eye rotates away from the projected line shaped laser beam, and the pupil position cannot be reconstructed directly from the measurement spectra anymore. As can be seen in FIG. 9, the practical eye tracking angles are limited to about +/−20 degrees. However, Doppler velocity signals will still be present. Integration of these velocity signals can be used to derive eye positions at even larger eye gaze angles.

In the experiment described above, the spectra were acquired with 8 kHz. For the reconstruction, 16 spectra have been analyzed. For the curve in FIG. 9, another 9 point median filter was applied. The resulting update rate is 18 ms, so 56 Hz.

In a refinement of the embodiment described before, the optics 20 for projecting the laser beam 22 as a patterned laser beam onto the eye E may be optimized in terms of a better focus position of the patterned laser beam 26 on the eye E. In the experiment described above, this focus position is on a line at a distance of 40 mm from the laser source 12 of the laser sensor 10. It would be preferred to have the best focus position as good as possible matching the position of the front surface of the eye for optimum SMI signals, i.e. the projected patterned laser beam 26 to be as best as possible focused along the curved line beam projected on the eye.

Figures 10, 11:
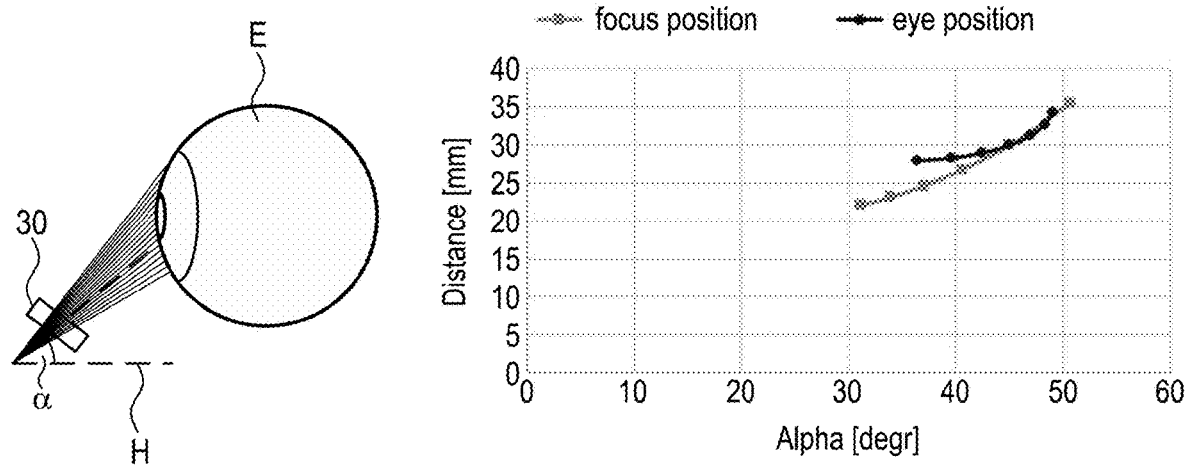
FIG. 10 shows a sketch similar to FIG. 6 with a tilted cylinder lens as optics of the laser sensor according to some embodiments.
FIG. 11 shows a graph of the distance of the eye in FIG. 10 to the laser sensor as a function of an angle α in FIG. 10, both for focus position and front position of the eye according to some embodiments.

FIG. 10 shows the front position of the eye E as a distance towards the laser source 12 of the laser sensor 10. $\alpha$ is the angle of the laser beam along the patterned line shaped beam 26 with respect to the horizontal axis H. At larger angles $\alpha$, the distance of the front of the eye E to the laser source 12 is larger. A similar effect can be obtained for the focus position by placing an f=5 mm cylinder lens 30 (as optics 20 in FIG. 1) at a 30° tilted position, wherein the distance of laser source to lens 30 for the central beam is 6.3 mm. Thus, using a tilted cylinder lens 30 enables to match the focus position better to the eye position as shown in FIG. 10. FIG. 11 shows the distance of the focus position to the laser source as a function of angle $\alpha$ both for the focus position and the front position of the eye.

This is only an example how the SMI signals may be optimized by a better focus position. Further optimizations may be done by using e.g. free form optics. In that way, also the Gaussian intensity distribution of the projected patterned laser beam can be transformed into a more homogenous pattern.

Crossed cylinder lenses at different distances to the laser source and with different magnification factors (optionally different focal lengths) can also be used to create an elongated focus. This way, also the amount of laser light collected back into the laser source may be optimized. This can also be one optical element with the two crossed cylinder lenses distributed on the two surfaces of the optical element. Alternatives to cylindrical or free-form lenses made of optical material like glass or polymer to create an appropriate beam focus are optical grating structures, like imprinted surface gratings, holographical optics like photopolymer hologram layers, or meta lenses. These kinds of structures may also be used to create e.g. a line of spots instead of a continuous line. Other shapes as a line may also be considered.

Figure 12:
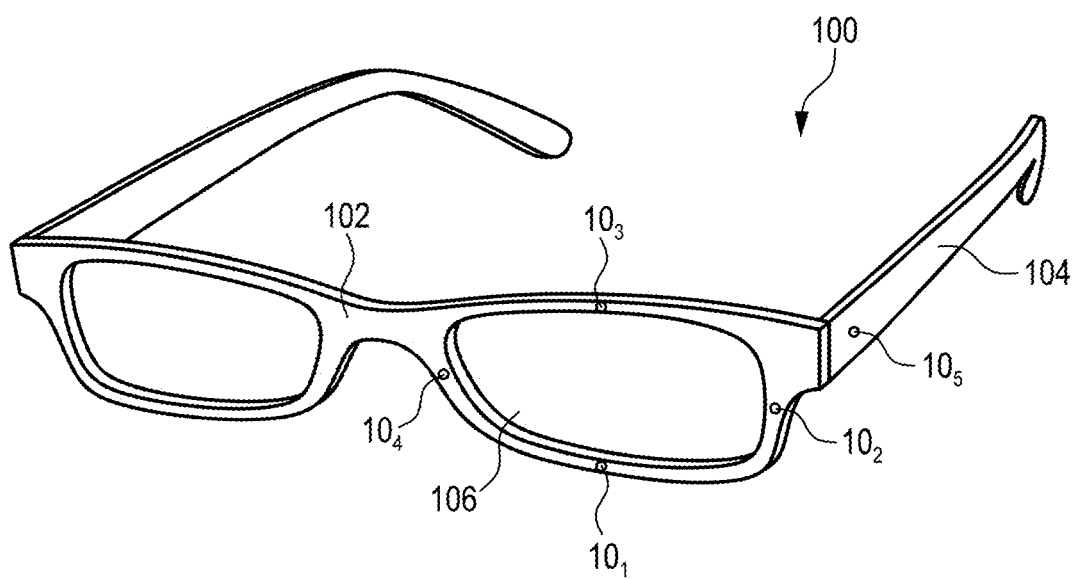
FIG. 12 shows spectacles with integrated laser sensors according to some embodiments.

FIG. 12 shows a system 100 which makes use of the teachings of the present disclosure according to an embodiment. System 100 is configured to detect the gaze of a human eye (not shown in FIG. 12). The system 100 is configured in form of spectacles 102 comprising a frame with frame temple 104 and glasses 106. The system 100 comprises laser sensors $10_1$, $10_2$, $10_3$, and $10_4$ arranged on the frame 104. It is to be noted here that the laser sensors $10_1$ to $10_4$ are arranged on the inner side of the frame 104 which faces the eye of the user wearing the spectacles. Each of the laser sensors $10_1$ to $10_4$ may be configured as described above with reference to FIG. 1. The number of laser sensors may be less than four, wherein two laser sensors, e.g. laser sensors $10_1$ and $10_2$ may be sufficient for eye gaze angle detection. A further laser sensor $10_5$ may be arranged on the frame temple 104 to measure extreme eye rotations. Some or all the laser sensors $10_1$ to $10_5$ could also be integrated in one or both of the spectacle's glasses 106 or in the nose pads. In one further possible embodiment, the laser sensors $10_1$ to $10_4$ may be arranged in the frame temple, but could emit the laser beams towards the glasses 106, wherein a holographic optical element embedded in the glasses may deflect the laser beams towards the eye. In another embodiment, both the left and the right eye can be tracked simultaneously, using e.g. two sensors per eye.

The system 100 may be operated in different modalities. In a first modality, the laser sources of the laser sensors $10_1$ to $10_4$ may be operated at continuous waves (constant frequencies). In a second modality, the frequency of the laser sources may be modulated in time, e.g. following a triangular modulation pattern as described above.

With reference to FIGS. 13 to 16, an embodiment of the system for eye gaze angle detection will be described which is modified with respect to the above embodiments described with respect to FIGS. 5 to 9.

Figure 13:
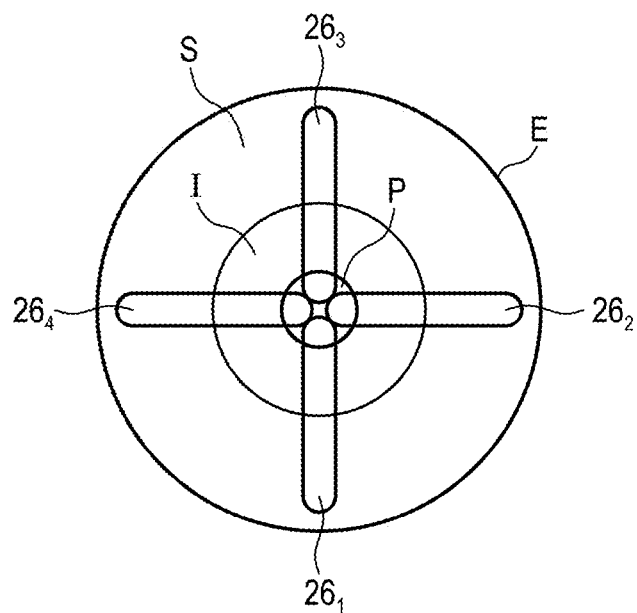
FIG. 13 shows a front view of a human eye with laser beams of four laser sensors which are projected as patterned laser beams on the surface of the eye according to some embodiments.

FIG. 13 shows, similar to FIG. 5, a front view of a human eye E. FIG. 13 shows four projected patterned laser beams $26_1$, $26_2$, $26_3$, $26_4$, which are emitted by the laser sensors $10_1$, $10_2$, $10_3$, and $10_4$. The projected patterned laser beams $26_1$ to $26_4$ may be formed by optics like optics 20, e.g. a cylinder lens or holographical optical element, to fit the desired shape of the sensing region on the eye E. Each of the projected patterned laser beams $26_1$, $26_2$, $26_3$, $26_4$ forms a corresponding sensing region. In this example, four laser sensors, e.g. ViP sensors, are used with a cylinder lens to form the corresponding sensing region. The projected patterned laser beams $26_1$ to $26_4$ are stripes arranged in a two-dimensional pattern, e.g. forming a cross. It is, however, to be understood that other possible patterns of the projected laser beams are conceivable, e.g. circles, rectangles, grids, etc. In addition, adding more laser sensors increases the sensing surface size and therefore the coverable field of view. Less laser sensors can be used to reduce the overall power consumption. Due to the high temporal resolution of the sensor principle, time multiplexing can be used to decrease the power consumption of the necessary electronics and the optical power on the eye surface to fulfill eye safety considerations.

As described above, the laser sensors $10_1$ to $10_4$ measure distances towards the eye surface and velocities of the eye surface in the corresponding sensing region corresponding to the patterned laser beams $26_1$ to $26_4$. In addition, the signal to noise ratio (SNR) may be determined from the measurement data to obtain information about the part of the eye (sclera S, iris I, pupil P) currently illuminated by the respective projected patterned laser beam $26_1$ to $26_4$.

Figure 14A:
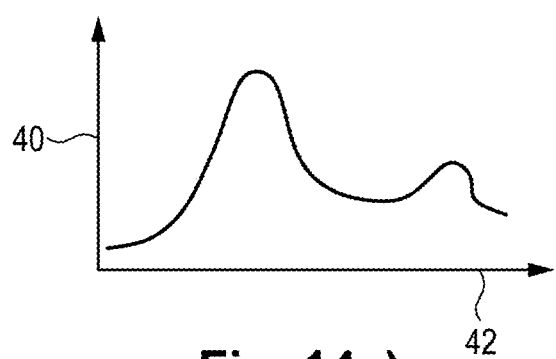
FIG. 14a) and FIG. 14b) show measured frequency spectra for two sensing regions on the surface of the eye in the rotational position according to FIG. 13, wherein FIG. 14a) shows a corresponding frequency spectrum of the first sensing region and FIG. 14b) shows a frequency spectrum of another sensing region, according to some embodiments.
Figure 14B:
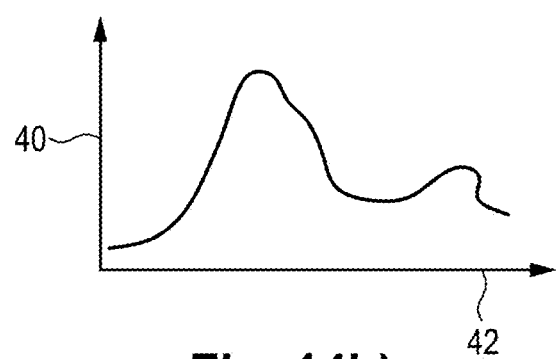

FIGS. 14a) and 14b) show in simplified manner frequency spectra measured by the two laser sensors $10_4$ and $10_2$ in FIG. 12 for an eye position as shown in FIG. 13. The y-axis 40 shows the signal amplitude in relation to the frequency on the x-axis 42. FIG. 14a) shows the frequency spectrum in the sensing region of projected patterned laser beam $26_4$, and FIG. 14b) shows the frequency spectrum in the sensing region of projected patterned laser beam $26_2$. As the eye in FIG. 4 is centered with respect to the four sensing regions $26_1$ to $26_4$, the amplitude distribution in both SMI frequency spectra is similar, representing similar distance patterns.

If the eye E is rotated towards the sensing region corresponding to the projected patterned laser beam $26_2$, as shown in FIG. 15, the Fourier spectrum of the SMI signal varies. The corresponding amplitude distribution (Fourier spectrum) changes accordingly due to the rotation of the eye E. FIGS. 16a) and 16b) show the changed amplitude distributions of the Fourier spectra in the two sensing regions $26_4$ and $26_2$ after eye rotation. The frequency spectra can be understood as a depth probability distribution. If the sensor region covers only a spot on a flat surface, the spectrum contains only a single peak at the frequency representing the optical path length between laser sensor and flat surface. If the laser spot is widened up as it is the case with the projected patterned laser beams $26_1$ to $26_4$, and aims at a step-like surface with two distinct distances, the spectra will represent this by two peaks representing both distance levels. Depending on power distribution towards both surfaces, amplitude relation of both peaks will represent the integral power relation of both surface regions. The laser sensor which covers sensing region $26_2$ measures a higher fraction of the iris and pupil region of the eye E. As a significant amount of photons enter through the pupil into the eye E to the retina, and hence produce SMI data correlating with an increased optical path length into the eye, this leads to an increase of the amplitudes for higher frequencies correlating with the retinal distance. On the other hand, the amplitude at high frequencies correlating with retinal distance measured by the laser sensor in the sensing region $26_4$ decreases, as the photons are scattered by closer surface fractions of the eye like sclera and iris.

To calculate the pupil position and the gaze direction, the difference between the laser sensor signals obtained from different sensing regions can be used. Additional SMI information acquired by the laser sensors, like SNR or velocity, can be used to improve the system accuracy. Based on the measured time series, additional features like pupil size can be extracted from the laser sensor signals. With this information, an additional improvement of the accuracy of the pupil position estimation can be achieved. Other features that can be used to improve the system accuracy are full width half-maximum peak width or amplitude of spectral data or information from the time domain signal (e.g. thresholds, time differences, etc.).

In eye gaze angle detection, eye lashes may (partially) block the projected patterned laser beam, and consequently the signal quality may be reduced. Because the lashes provide signals from a closer distance, these false signals occurring at low frequencies in the frequency spectrum can be discarded from the real signals from the eye when looking at the frequency spectra.

An alternative to solve the eye lashes issue will be described with reference to FIG. 19.

Figure 19:
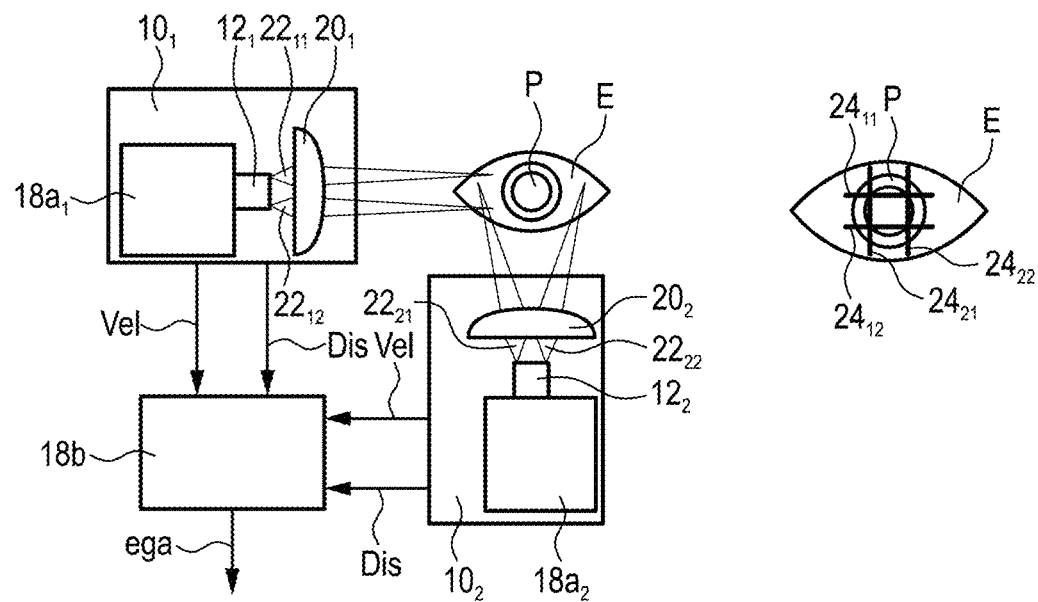
FIG. 19 shows another embodiment of a system for eye gaze angle detection according to some embodiments.

FIG. 19 shows a system for eye gaze angle detection which comprises laser sensors $10_1$ and $10_2$. Laser sensor $10_1$ comprises a laser source $12_1$ which may be a VCSEL with integrated photodiode (ViP). The laser source $12_1$ emits two (or more) laser beams $22_{11}$ and $22_{12}$. In case the laser source $12_1$ comprises a ViP, the ViP may comprise two (or more) laser emission regions, e.g. two (or multiple) mesas. The laser beams $22_{11}$ and $22_{12}$ are preferably emitted in a time-multiplexed manner. Optics $20_1$ project the emitted laser beams $22_{11}$ and $22_{12}$ as patterned laser beams $24_{11}$ and $24_{12}$ in form of two line beams onto the eye E, as shown in the right-hand side diagram. The projected patterned laser beams $24_{11}$ and $24_{12}$ are projected at slightly shifted positions on the surface of the eye E. The optics $20_1$ may be a single optical element, for example a cylinder lens, as described above. A controller 18 (e.g. an ASIC) including a pre-processing algorithm receives electrical signals provided by the detector integrated into the laser source $12_1$ which are caused by self-mixing interference of laser-light re-entering the laser cavity of the laser source $12_1$. Pre-processing the electrical signals in controller $18a_1$ includes extracting from the frequency spectrum velocity distribution information Vel and distance distribution information Dis, wherein the velocity and distance distribution information is output to a controller 18b which includes a post-processing algorithm (e.g. analytical/neural network) and outputs the eye gaze angle 'ega' measured in the horizontal direction. The laser sensor $10_2$ may have the same configuration as the laser sensor $10_1$, except that laser beams $22_{21}$ and $22_{22}$ emitted by the laser source $12_2$ are projected by optics $20_2$ as patterned laser beams $24_{21}$ and $24_{22}$ onto the eye E to measure the eye gaze angle in the vertical direction. Again, velocity distribution information Vel and distance distribution information Dis is output from laser sensor $10_2$ to the controller 18b so that in combination with the velocity and distance distribution information from the laser source $10_1$, the 2D eye gaze angle of the eye E can be accurately measured.

The embodiment described with reference to FIG. 19 enhances the chance that one of the projected laser beams $24_{11}$ and $24_{12}$ hits the eye E, without being (partially) blocked by the lashes of the eye E. The same holds for the two projected laser beams $24_{21}$ and $24_{22}$. Thereby, an improved accuracy for the eye gaze angle detection is obtained.

The laser sensors $10_1$ and $10_2$ may be arranged integrated in spectacles, as described above with reference to FIG. 12.

Figure 20:
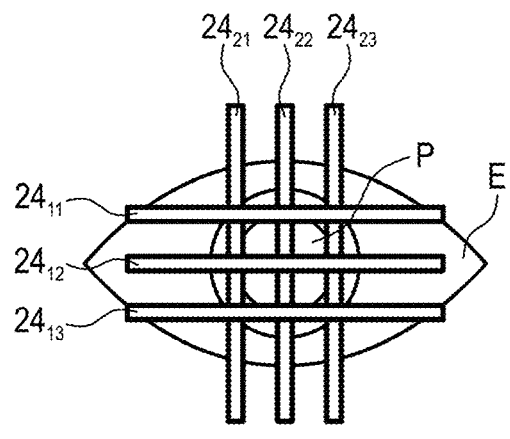
FIG. 20 shows a modification of a patterned beam projected onto an eye according to some embodiments.

A further modification of the previous embodiment may use multiple projected patterned laser beams, as shown in FIG. 20. FIG. 20 shows projected patterned laser beams $24_{11}$, $24_{12}$, $24_{13}$ and $24_{21}$, $24_{22}$ and $24_{23}$ projected onto the eye E. Using multiple projected laser beams, e.g. with a pattern in form of a grid of lines as shown not only is beneficial in case of lashes, but it can also be used to cover a larger area on the eye E so that there are more chances to see the pupil position in one of the laser beam lines. As already described above, other shapes of patterned laser beams than straight lines as shown in FIG. 20 may be used.

In the embodiment of FIG. 20, time-multiplexing can also be used to know from which laser beam line the signal comes in case of using a laser source with multiple laser emission regions and one photodiode only.

Figure 21:
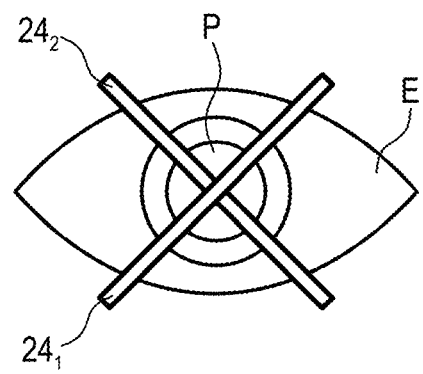
FIG. 21 shows another modification of a patterned beam projected onto an eye according to some embodiments.

Another advantage of projecting patterned laser beams as shown in FIG. 19 and FIG. 20 is strongly reduced visibility of the laser light, because the irradiance (W/m$^2$) on the retina reduces as compared to a system which projects a point-like spot on the eye. It is to be noted here that the human eye may see laser light even in a wavelength range from 750 to 950 nm. The laser beam projected onto the eye thus may disturb the user. Furthermore, it was observed in experiments that a laser beam line in horizontal direction is more visible to the user as compared to a laser beam line in vertical direction. In order to reduce visibility of the projected laser beam or laser beams, it is therefore beneficial to project the laser beam or laser beams onto the eye E in a diagonal line pattern, as shown in FIG. 21 for two laser beam lines $24_1$ and $24_2$. In another example, the laser beam line pattern in FIG. 20 may be rotated by 45° as well.

Figure 17:
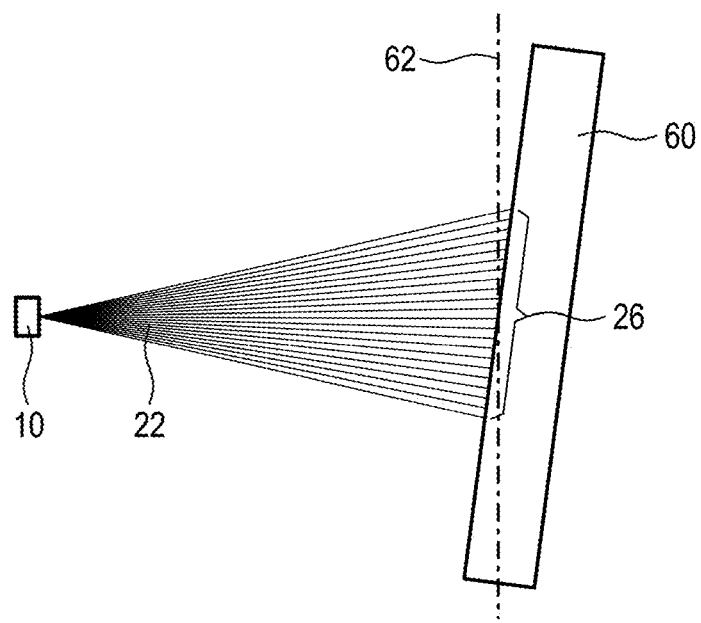
FIG. 17 shows a laser sensor for use in measuring tilt of an object according to some embodiments.

A system comprising a laser sensor like laser sensor 10 in FIG. 1 making use of the principles of the present disclosure may also be configured for tilt detection, i.e. for detecting or measuring a tilt of an object, as shown in FIG. 17 for an object 60 which is tilted with respect to a reference, e.g. a vertical axis 62. Tilt detection is already enabled by one laser sensor 10 according to the principles of the present teachings, by projecting a laser beam 22 as a one- or two-dimensional patterned laser beam 26 onto the object 60 such that a distance of the patterned laser beam 26 from the laser source of the laser sensor 10 varies along the patterned laser beam 26 projected on the object 60, and spectrally analyzing the SMI signal and extracting from the spectrum of the SMI signal multiple frequencies indicative of multiple distances along the patterned laser beam from the laser source. The laser beam 22 may be wavelength modulated as described above, for example a triangle modulation of the laser beam 22 may be used. In case the object 60 does not have a tilt, the spectral width of the frequencies after FFT is minimal. When the object tilts, a broadening of the spectrum will occur, wherein the broadening increases with increasing tilt.

Tilt detection may also be used for eye gaze tracking. This is because the iris is a relatively flat part of the eye. Thus, when the eye is rotated away from the center position, the corresponding tilt of the iris can be observed in the SMI signal. Thus, tilt of the iris is a measure for the eye gaze angle. Sign information of the tilt may be derived by the observed Doppler frequencies.

Tilt detection and eye gaze tracking can be performed by extracting features from the frequency spectrum of the SMI signal, as its width, or by fitting a function to the spectrum (template matching) or by using neural networks.

One algorithm embodiment for tilt/eye gaze angle detection may consist of the following stages:
1) Recording time domain SMI signal, preferably with modulation of the laser beam,
2) transforming time-domain signal to frequency domain using FFT algorithm,
3) extracting features from the spectrum (e.g. width at half peak maximum or transformation parameters of a template matching algorithm),
4) mapping function from feature vector to tilt/eye angle.

Figure 18:
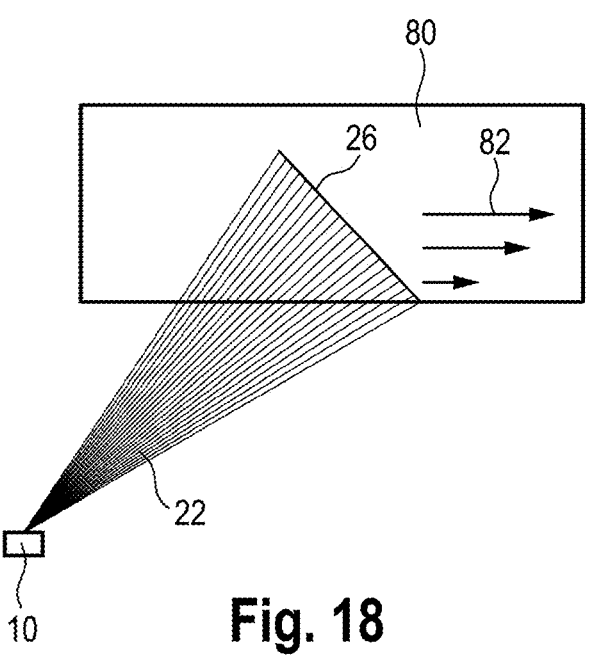
FIG. 18 shows a laser sensor for use in detecting a velocity profile in a fluid according to some embodiments.

A system comprising a laser sensor like laser sensor 10 in FIG. 1 may also be configured to detect a velocity profile of a flowing fluid. FIG. 18 shows a sketch of a system configured to detect a velocity profile of a flowing fluid 80. The velocity profile is illustrated by arrows 82, wherein the lengths of the arrows indicate the local velocity along the cross-section of the flowing fluid 80. A laser sensor 10 emits a laser beam 22 which is projected into the fluid as a patterned one- or two-dimensional laser beam as described above. Micro-particles typically present in the fluid 80 scatter back the laser light from the position of the projected patterned laser beam 26 in the fluid 80 so that laser light from the position of the projected patterned laser beam 26 re-enters the laser source. Modulation of the emitted laser beam 22 is not necessarily required in this embodiment. It is preferred to have SMI signals from the focus position at the location of the projected patterned laser beam 26 only so that for this embodiment it is preferred to have a relatively large numerical aperture at the fluid side for optimal position discrimination. The strongest SMI signals will originate from the focus position, being at different positions in the fluid along the patterned laser beam 26. Thereby, it is possible to determine the velocity profile in the fluid.

Generally, the principles of the present disclosure provide instead of one velocity and one distance as it is the case for normal SMI, a range of velocities and distances. Those skilled in the art will be able to make more applications based on the same SMI measurement principles of a patterned laser beam in combination with a spectral analysis.

As follows from the above description, the present disclosure also encompasses a method of detecting a plurality of velocities and/or distances, wherein the method comprises: emitting a laser beam 22 from a laser source 12, projecting the laser beam 22 as a one- or two-dimensional patterned laser beam 26 onto an object to be examined, such that a distance of the patterned laser beam 26 from the laser source 12 varies along the patterned laser beam 26 projected on the object, determining a self-mixing interference signal generated by laser light of the patterned laser beam 26 reflected by the object back into the laser source 12, and spectrally analyzing the self-mixing interference signal and extracting from the spectrum of the self-mixing interference signal multiple frequencies indicative of multiple distances of portions of the object from the laser source 12, and/or multiple velocities of portions of the object with respect to the laser source 12.

The teachings herein also encompass a computer program product, comprising program code means for causing a laser sensor like laser sensor 10 or a system like system 100 to carry out the steps of the method indicated before, when said computer program is carried out on a processor of the laser sensor or on a processor of the system.

A computer program may be stored/distributed on a suitable non-transitory medium, such as an optical storage medium or a solid-state medium supplied together with or as part with other hardware that may also be distributed in other forms, such as via the internet or other wired or wireless telecommunication systems.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:
1. A laser sensor, comprising:
a laser source configured to emit a laser beam, optics configured to project the laser beam as a one-or two-dimensional patterned laser beam onto a surface of an object to be examined, such that a distance of the patterned laser beam from the laser source varies for different regions of the surface onto which the patterned laser beam is projected, a detector configured to determine a self-mixing interference signal generated by laser light of the patterned laser beam reflected from the object back into the laser source, and circuitry configured to analyze a single spectrum of the self-mixing interference signal and extract from the single spectrum of the self-mixing interference signal multiple frequencies indicative of at least one of the following: multiple distances of the different regions of the surface from the laser source, or multiple velocities of the different regions of the surface with respect to the laser source.

2. The laser sensor of claim 1, wherein the multiple frequencies are indicative of the multiple distances of the different regions of the surface from the laser source.

3. The laser sensor of claim 1, wherein the multiple frequencies are indicative of the multiple velocities of the different regions of the surface with respect to the laser source.

4. The laser sensor of claim 1, further comprising an electrical driver configured to provide a driving current to the laser source to cause the laser source to emit the laser beam, wherein the electrical driver is configured to provide a modulated driving current to the laser source to cause the laser source to emit the laser beam with a periodically varying wavelength.

5. The laser sensor of claim 1, wherein the optics is configured to project the laser beam with a pattern onto the object, which is selected from the group consisting of a continuous-line pattern, a dot-line pattern, a multiple-line pattern, and a two-dimensional area pattern.

6. The laser sensor of claim 1, wherein the optics is further configured to focus the patterned laser beam on the object.

7. The laser sensor of claim 1, wherein the optics is selected from the group consisting of a single cylinder lens, two or more crossed cylinder lenses, a cylinder lens having cylindrical surfaces with different orientations of cylinder axes of the cylindrical surfaces, free form optics, meta optics, diffractive optics, holographical optics, fully or partially reflecting spherical, and cylindrical or free-form mirrors.

8. A system for detecting at least one of a position or velocity of an object, the system comprising a laser sensor according to claim 1.

9. The system of claim 8, further comprising at least a second laser sensor, the second laser sensor comprising:

a second laser source configured to emit a second laser beam, and second optics configured to project the second laser beam as a second patterned laser beam onto the object, wherein the patterned laser beam and the second patterned laser beam intersect on the object with a non-zero angle.

10. The system of claim 8, wherein the object is a human eye, and the circuitry is configured to detect a gaze angle of the human eye from the self-mixing interference signal.

11. The system of claim 10, wherein the laser sensor is arranged on or integrated into spectacles to be worn in front of the human eye.

12. The system of claim 10, wherein the circuitry is configured to determine the gaze angle of the human eye from a gap in the single spectrum of the self-mixing interference signal between low and high frequencies.

13. The system of claim 8, wherein the circuitry is configured to detect a tilt angle of the object from the self-mixing interference signal.

14. The system of claim 13, wherein the object is the iris of a human eye, and wherein the circuitry is configured to determine a gaze angle of the human eye from the tilt angle of the iris.

15. The system of claim 8, wherein the object is a flowing fluid, and the circuitry is configured to detect a velocity profile of the flowing fluid from the self-mixing interference signal.

16. A method comprising:

emitting a laser beam from a laser source, projecting the laser beam as a one-or two-dimensional patterned laser beam onto a surface of an object to be examined, such that a distance of the patterned laser beam from the laser source varies for different regions of the surface onto which the patterned laser beam is projected, determining a self-mixing interference signal generated by laser light of the patterned laser beam reflected from the object back into the laser source, and analyzing a single spectrum of the self-mixing interference signal and extracting from the single spectrum of the self-mixing interference signal multiple frequencies indicative of at least one of the following: multiple distances of the different regions on the surface from the laser source, or multiple velocities of the different regions of the surface with respect to the laser source.

17. A non-transitory computer-readable medium having program code stored thereon, the program code, when executed by one or more processors, causing a laser sensor or a system to carry out the following steps:

emitting a laser beam from a laser source, projecting the laser beam as a one-or two-dimensional patterned laser beam onto a surface of an object to be examined, such that a distance of the patterned laser beam from the laser source varies for different regions of the surface onto which the patterned laser beam is projected, determining a self-mixing interference signal generated by laser light of the patterned laser beam reflected from the object back into the laser source, and analyzing a single spectrum of the self-mixing interference signal and extracting from the single spectrum of the self-mixing interference signal multiple frequencies indicative of at least one of the following: multiple distances of the different regions of the surface from the laser source, or multiple velocities of the different regions of the surface with respect to the laser source.

* * * * *